(12) United States Patent
Kim et al.

(10) Patent No.: US 10,851,044 B2
(45) Date of Patent: Dec. 1, 2020

(54) METHOD FOR PREPARING GLUTAMATE-BASED SURFACTANT

(71) Applicant: AK CHEMTECH CO., LTD., Seoul (KR)

(72) Inventors: Byung Jo Kim, Daejeon (KR); Ki Ho Park, Daejeon (KR); Hyon Pil Yu, Daejeon (KR); Ji Hye Bae, Daejeon (KR); Song Yi Kim, Daejeon (KR)

(73) Assignee: AK CHEMTECH CO., LTD., Seoul (KR)

( * ) Notice: Subject to any disclaimer, the term of this patent is extended or adjusted under 35 U.S.C. 154(b) by 0 days.

(21) Appl. No.: 16/651,987

(22) PCT Filed: Sep. 21, 2018

(86) PCT No.: PCT/KR2018/011259
§ 371 (c)(1),
(2) Date: Mar. 27, 2020

(87) PCT Pub. No.: WO2019/066412
PCT Pub. Date: Apr. 4, 2019

(65) Prior Publication Data
US 2020/0255370 A1      Aug. 13, 2020

(30) Foreign Application Priority Data
Sep. 29, 2017   (KR) .................. 10-2017-0127059

(51) Int. Cl.
| | | |
|---|---|---|
| *C07C 227/28* | (2006.01) | |
| *C07C 227/40* | (2006.01) | |
| *C11D 1/10* | (2006.01) | |
| *C07C 229/24* | (2006.01) | |
| *C07C 229/76* | (2006.01) | |

(52) U.S. Cl.
CPC .......... *C07C 227/28* (2013.01); *C07C 227/40* (2013.01); *C07C 229/24* (2013.01); *C11D 1/10* (2013.01); *C07C 229/76* (2013.01)

(58) Field of Classification Search
CPC ... C07C 227/28; C07C 227/40; C07C 229/24; C07C 229/76; C11D 1/10
See application file for complete search history.

(56) References Cited

U.S. PATENT DOCUMENTS

2004/0063980 A1 * 4/2004 Raths ................. C11D 1/52
554/69
2013/0030198 A1    1/2013 Harichian et al.

FOREIGN PATENT DOCUMENTS

KR          890000536 B1      3/1989

OTHER PUBLICATIONS

Zhang, G. et al., Green synthesis, composition analysis and surface active properties of sodium cocoyl glycinate, American Journal of Analytical Chemistry, vol. 4, No. 9, pp. 445-450 (Year: 2013).*
Foley, P. et al., "Derivation and synthesis of renewable surfactants," Chemical Society Reviews, vol. 41, No. 4, Feb. 21, 2012, Available Online Oct. 17, 2011, 22 pages.
Zhang, G. et al., "Green Synthesis, Composition Analysis and Surface Active Properties of Sodium Cocoyl Glycinate," American Journal of Analytical Chemistry, vol. 4, No. 9, Sep. 2013, 6 pages.
ISA Korean Intellectual Property Office, International Search Report Issued in Application No. PCT/KR2018/011259, Feb. 25, 2019, WIPO, 4 pages.

* cited by examiner

*Primary Examiner* — Yate' K Cutliff
(74) *Attorney, Agent, or Firm* — McCoy Russell LLP

(57) ABSTRACT

The present invention relates to a method for preparing a glutamate-based surfactant. More specifically, the present invention provides a method for preparing a glutamate-based surfactant, the method being very economical and being capable of mass production of the glutamate-based surfactant.

11 Claims, No Drawings

METHOD FOR PREPARING GLUTAMATE-BASED SURFACTANT

CROSS-REFERENCE TO RELATED APPLICATIONS

The present application is a U.S. National Phase of International Patent Application Serial No. PCT/KR2018/011259 entitled "METHOD FOR PREPARING GLUTAMATE-BASED SURFACTANT," filed on Sep. 21, 2018. International Patent Application Serial No. PCT/KR2018/011259 claims priority to Korean Patent Application No. 10-2017-0127059 filed on Sep. 29, 2017. The entire contents of each of the above-referenced applications are hereby incorporated by reference for all purposes.

TECHNICAL FIELD

The present invention relates to a method for preparing a glutamate-based surfactant, and more particularly, to a method for preparing a glutamate-based surfactant which effectively removes an inorganic salt produced during preparation of the glutamate-based surfactant to simplify a preparation process and reduce manufacturing costs.

BACKGROUND ART

A surfactant is a compound having both a hydrophilic group and a lipophilic group in one molecule, and is present in a natural ecosystem or prepared by synthesis, and there are more than tens of thousands kinds thereof. The surfactant has functions such as emulsification, solubilization, cleaning, dispersing, moisturization, foaming, an antistatic function, and sterilization, and is utilized in various fields of industry such as detergents, fibers, cosmetics, pharmaceuticals, foods, paints, pesticides, paper manufacture, mining, lubricants, civil engineering, construction, rubbers, plastics, oil extraction, and soil regeneration. In particular, the surfactant is contained as a main component in household and industrial detergents which are used for hygiene and cleanliness, and plays a key role such as cleaning.

The surfactant should satisfy various requirements for being used in household and industrial detergents. That is, since the detergent is used in a large amount and relatively inexpensive, the surfactant used therein should be also mass-produced at an economic cost. In addition, since the detergent may be in contact with the human body in the course of use and is discharged with water through sewage after use, the detergent should not cause toxicity and irritation at the time of being in contact with and absorbed by the human body during use, and should be easily decomposed by sewage treatment equipment and in a natural ecosystem even when discharged through sewage, thereby having a less influence on a water environment.

Besides, in recent developments of the surfactant, various approaches have been attempted in terms of resource and energy saving as well as basic performance of the surfactant, economic feasibility, and safety to the human body and the environments.

DISCLOSURE

Technical Problem

An object of the present invention is to provide a method for preparing a glutamate-based surfactant, which may effectively reduce manufacturing costs by a simple process to allow mass production.

Technical Solution

The present invention provides a method for preparing a glutamate-based surfactant, which separates and purifies a reaction mixture by a simple process during a manufacturing process of a glutamate-based surfactant to dramatically improve manufacturing equipment and manufacturing costs, and in one general aspect, a method for preparing a glutamate-based surfactant includes:

(a) subjecting a triglyceride derivative to a chlorination addition reaction to be chlorinated;

b) reacting a product from a) with a glutamic acid salt to prepare a reaction mixture;

(c) adding an acid aqueous solution to the reaction mixture from b) to separate layers; and d) purifying an organic layer separated from c) with a 4% or more inorganic salt aqueous solution to prepare the glutamate-based surfactant.

Preferably, the inorganic salt aqueous solution according to an exemplary embodiment of the present invention may be a 4 wt % to 20 wt % solution, and an inorganic salt of the inorganic salt aqueous solution may be any one or two or more selected from NaCl, $Na_2SO_4$, $NaNO_3$, and $Na_3PO_4$.

The acid aqueous solution according to an exemplary embodiment of the present invention may be an aqueous solution including any one or two or more acids selected from sulfuric acid, hydrochloric acid, phosphoric acid, and nitric acid, and the inorganic salt aqueous solution may have a specific gravity of 1.03 or more.

Preferably, the purification according to an exemplary embodiment of the present invention may be performed by layer separation after stirring at 60° C. to 95° C., and the step b) may be performed at 0° C. to 20° C. and pH 12 to 14.

Preferably, in the step b) according to an exemplary embodiment of the present invention, the glutamic acid salt may be used in a range of 1.0 mol to 2.0 mol, based on 1 mol of the triglyceride derivative.

Preferably, the triglyceride derivative according to an exemplary embodiment of the present invention may be obtained from one or more triglyceride-containing materials selected from shea butter, cupuacu butter, mango butter, pitch butter, lime butter, argan butter, jojoba butter, coffee butter, cocoa butter, pistachio butter, rice butter, vegetable lanolin butter, olive butter, camellia butter, aloe butter, vanilla butter, avocado butter, hemp seed butter, illipe butter, kokum butter, mochaccino butter, murumuru butter, shea aloe butter, and sweet almond butter.

Preferably, the chlorination addition reaction of the present invention may be performed by reacting 1 mol of the triglyceride derivative with 1.0 mol to 2.0 mol of a chlorinated acylating agent, and performed with one or more chlorinated compounds selected from phosphorus pentachloride, phosphorus trichloride, and sulfonyl chloride (I).

Advantageous Effects

The method for preparing a glutamate-based surfactant of the present invention does not need additional reaction equipment and additional heating equipment, and thus, is very economical and efficient, and allows easy mass production.

In addition, the method for preparing a glutamate-based surfactant of the present invention minimizes unreacted material residues by having high reactivity, and may produce a glutamate-based surfactant having a high purity, in spite of no need for a complicated purification process.

Accordingly, since the glutamate-based surfactant prepared from the preparation method of the present invention has excellent physicochemical properties such as foamability, detergency, and biodegradability as well as solubility in water, it may be used instead of synthetic surfactants which are mainly used in the existing industrial sites, and furthermore, since the glutamate-based surfactant has low irritation to the human body, it may be applied to very diverse fields such as cosmetics, soaps, detergents, and shampoos, in which the surfactants are brought into contact with the human body a lot.

BEST MODE

Hereinafter, the method for preparing a glutamate-based surfactant of the present invention will be described, however, technical terms and scientific terms used herein have the general meaning understood by those skilled in the art to which the present invention pertains unless otherwise defined, and a description for the known function and configuration which may unnecessarily obscure the gist of the present invention will be omitted in the following description.

The method for preparing a glutamate-based surfactant of the present invention includes:
 a) subjecting a triglyceride derivative to a chlorination addition reaction;
 b) reacting a product from a) with a glutamic acid salt to prepare a reaction mixture;
 c) adding an acid aqueous solution to the reaction mixture from b) to separate layers; and
 d) purifying an organic layer separated from c) with a 4% or more inorganic salt aqueous solution to prepare the glutamate-based surfactant.

Unlike other amino acid-based surfactants, in the case of the glutamate-based surfactant, a specific gravity of an organic layer including the glutamate-based surfactant produced in a purification process is higher than that of an aqueous layer including an inorganic salt present as a reaction by-product, so that the organic layer including the glutamate-based surfactant is positioned below the aqueous layer.

Accordingly, separate equipment for removing the aqueous layer including the inorganic salt is needed and the process becomes complicated to increase manufacturing costs and make the mass production thereof difficult.

Thus, the present inventors conducted various research in order to overcome the problem, and improved the existing problems by adding a 4 wt % or more inorganic salt aqueous solution to the prepared organic layer including the glutamate-based surfactant to perform purification by layer separation.

Specifically, in the method for preparing a glutamate-based surfactant of the present invention, a triglyceride derivative is subjected to a chlorination addition reaction and then reacted with a glutamic acid salt to prepare a glutamate-based anionic surfactant, and an inorganic salt aqueous solution including an inorganic salt having a controlled content is added in a purification step of removing an inorganic salt included as a reaction by-product to increase a specific gravity of an aqueous layer, thereby easily removing the inorganic salt, and thus, a preparation process may be simplified since additional equipment is not needed.

More specifically, though for removing an inorganic salt (as an example, NaCl) produced as a by-product after subjecting the triglyceride derivative according to an exemplary embodiment of the present invention to a chlorination addition reaction and then to an acylation reaction with a glutamic acid salt, washing with water, preferably ionized water, should be performed, an acylation reaction product is dissolved in ionized water, so that the reaction product may not be separated from an aqueous layer including the inorganic salt.

Thus, the acylation reaction product should be converted into a state insoluble in ionized water (an organic acid state). Here, an acid (as an example, sulfuric acid ($H_2SO_4$)) may be added (precipitation) to convert the acylation reaction product into an organic acid state insoluble in ionized water, and when washed with ionized water, a layer separation phenomenon with an ionized water layer is used to wash the inorganic salt.

Here, the sulfuric acid ($H_2SO_4$) added is also converted into an inorganic salt ($Na_2SO_4$) by a high pH (pH 12 to 14) of the acylation reaction product, and the inorganic salt is also removed together with NaCl as a by-product by ionized water washing.

The acyl glutamate reaction product retains strong alkalinity by a reaction condition ($12 \leq pH \leq 14$), and sulfuric acid ($H_2SO_4$) is used for washing the inorganic salt with ionized water to convert the acyl glutamate reaction product into an organic acid which is insoluble in water when washed with ionized water.

When the product is converted into an organic material after adding sulfuric acid, the sulfuric acid added is converted into $Na_2SO_4$, and the specific gravity of the ionized water for washing is increased together with NaCl produced in the acylation reaction, to position the ionized water (wash water) layer in a lower layer of a batch reactor, whereby the ionized water layer is removed by a valve positioned in a lower portion of the batch reactor, and an organic layer including the glutamate-based surfactant converted into an organic material is present inside the reactor.

Thereafter, additional washing is performed three times using only ionized water, then the inorganic salt ($Na_2SO_4$, NaCl, and the like) still remaining in a small amount in the organic layer including the glutamate-based surfactant is removed, a small amount of the inorganic salt in the ionized water (wash water) layer is positioned in an upper portion of the batch reactor because the specific gravity of the organic layer including the glutamate-based surfactant becomes lower than the specific gravity of the ionized water (wash water) layer. Thus, it is not easy to remove the ionized water (wash water) layer from the batch reactor, and besides, due to a high melting point (60° C. to 70° C.) of the organic layer including the glutamate-based surfactant, when the organic layer including the glutamate-based surfactant is discharged to the outside of the batch reactor, a problem of hardening the organic layer including the glutamate-based surfactant causes significant time and utility (heating) loss.

Accordingly, the present inventors repeated the research, and found that when the organic layer including the glutamate-based surfactant prepared is purified, an aqueous solution including a controlled inorganic salt is added to increase the specific gravity of the aqueous solution (wash water) layer including the inorganic salt rather than the specific gravity of the organic layer including the glutamate-based surfactant and position the aqueous solution (wash water) layer including the inorganic salt in the lower portion of the reactor, thereby removing only the aqueous solution (wash water) layer including the inorganic salt from the outside of the batch reactor (preferably the lower portion of the reactor), while leaving the organic layer including the glutamate-based surfactant in the batch reactor.

Preferably, the inorganic salt aqueous solution according to an exemplary embodiment of the present invention may be a 4 wt % to 20 wt % solution, and more preferably a 4 wt % to 10 wt % solution in terms of efficiency and economic feasibility of the preparation method, and the inorganic salt of the inorganic salt aqueous solution may be any one or two or more selected from NaCl, $Na_2SO_4$, $NaNO_3$, and $Na_3PO_4$.

The acid aqueous solution according to an exemplary embodiment of the present invention converts a reaction mixture into an organic acid form, and preferably may be an aqueous solution including any one or two or more acids selected from sulfuric acid, hydrochloric acid, phosphoric acid, and nitric acid, and the inorganic salt aqueous solution may have a specific gravity of 1.03 or more, and preferably 1.03 to 1.07, in terms of economic feasibility and purification efficiency.

Preferably, the method for preparing a glutamate-based surfactant according to an exemplary embodiment of the present invention may be applied to a batch reactor.

Purification which is performed with the 4 wt % or more inorganic salt aqueous solution, according to an exemplary embodiment of the present invention may be performed by layer separation after stirring at 60° C. to 95° C., and preferably, purification may be performed by a method in which the 4 wt % or more inorganic salt aqueous solution is added to the organic layer including the glutamate-based surfactant recovered by the layer separation, stirred at 80° C. to 95° C. for 10 minutes to 1 hour, allowed to stand for 30 minutes to 2 hours, and subjected to layer separation.

The purification process may be performed once or more.

The step b) according to an exemplary embodiment of the present invention, of reacting a product prepared by subjecting a triglyceride derivative to a chlorination addition reaction with a glutamic acid salt to prepare a reaction mixture may satisfy the following reaction condition:

0° C. ≤ reaction temperature ≤ 20° C.

12 ≤ pH ≤ 14

According to an exemplary embodiment of the present invention, unreacted material residues may be minimized with high reactivity, a final product may be obtained with high selectivity, and a complicated reaction process is not needed, and thus, the glutamate-based surfactant may be provided by a very economical method.

The triglyceride derivative according to an exemplary embodiment of the present invention may be obtained from one or more natural triglyceride-containing materials selected from shea butter, cupuacu butter, mango butter, pitch butter, lime butter, argan butter, jojoba butter, coffee butter, cocoa butter, pistachio butter, rice butter, vegetable lanolin butter, olive butter, camellia butter, aloe butter, vanilla butter, avocado butter, hemp seed butter, illipe butter, kokum butter, mochaccino butter, murumuru butter, shea aloe butter, and sweet almond butter, and in terms of including saturated or unsaturated fatty acid having 8 to 18 carbon atoms as a main component, a triglyceride derivative obtained from shea butter, jojoba butter, cocoa butter, olive butter, shea aloe butter, and the like is preferred, since it shows high reactivity with a glutamate salt and the glutamate-based surfactant prepared therefrom has excellent foam stability, and in particular, the triglyceride derivative obtained from cocoa butter is more preferred in the present invention, since it shows surprisingly improved interface properties, but the present invention is not limited thereto. Here, a triglyceride compound obtained from the natural triglyceride-containing material may be a single material or a mixture, but the mixture allows implementation of a more preferred effect in the interface properties and may minimize a reaction by-product with a surprisingly improved activity under the reaction condition described above.

The triglyceride derivative according to an exemplary embodiment of the present invention may include a triglyceride derivative represented by the following Chemical Formula 1:

[Chemical Formula 1]

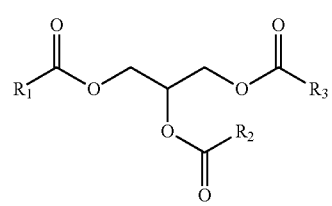

wherein $R_1$ to $R_3$ are independently of one another (C8-C30) alkyl or (C8-C30)alkenyl.

The "triglyceride derivative" described in the present invention may be a single material or a mixture. In addition, the triglyceride derivative obtained from a natural component is mostly in the state of a mixture, but has a triglyceride having one specific structure as a main component. Here, the main component refers to a component corresponding to 70 wt % or more, based on a total weight of the mixture.

In addition, alkyl described in the present invention refers to a linear or branched hydrocarbon, and alkenyl refers to a linear or branched hydrocarbon containing one or more double bonds. In addition, when the fatty acid compound according to the present invention has a hydrocarbon having 8 to 18 carbon atoms, foamability, foam stability, detergency, and the like are excellent without any influence on decreased solubility in water and preferred, but the fatty acid compound having a hydrocarbon having more than 18 carbon atoms is also included as an embodiment of the present invention.

According to an exemplary embodiment of the present invention, all of $R_1$ to $R_3$ of the triglyceride derivative may be (C8-C18)alkyl or (C8-C18)alkenyl, and in terms of high solubility in water, excellent emulsification and foam stability, and excellent workability and usability due to low viscosity with use at a high concentration, it is preferred that all of $R_1$ to $R_3$ are (C8-C18)alkyl.

According to an exemplary embodiment of the present invention, in the chlorination addition reaction, any chlorine acylating agent capable of chlorination may be used without limitation, of course, but a preferred example thereof may be one or more selected from phosphorus pentachloride, phosphorus trichloride, sulfonyl chloride (I), and the like, and the chlorine acylating agent added in an excessive amount may be easily volatilized and removed by vacuum distillation, and in terms of showing excellent reactivity during the chlorination addition reaction, it is more preferred to use phosphorus trichloride. Here, the chlorination addition reaction is performed without an additional solvent, and glycerol ($C_3H_5(OH)_3$), phosphorus acid ($H_3PO_3$), and the like produced as a by-product (lower portion) during the reaction may be layer-separated from the product after the reaction (upper portion) and simply removed after the reaction.

In addition, according to an exemplary embodiment of the present invention, a use amount of the chlorine acylating agent used in the chlorination addition reaction is not limited, but may be used in a range of 1.0 mol to 2.0 mol, based on 1 mol of the triglyceride derivative. Thus, preferably within a range not affecting reactivity, in terms of minimizing impurities due to unreacted materials, the chlorine acylating agent may be used in a range of 1.0 mol to 1.5 mol, but is not limited thereto.

According to an exemplary embodiment of the present invention, a chlorinated acyl compound prepared from the triglyceride derivative by the chlorination addition reaction is condensed with a glutamic acid salt with high reactivity, thereby providing a glutamate-based anionic surfactant showing excellent biodegradability and low irritation to the human body.

In the step of reacting with glutamic acid salt according to an exemplary embodiment of the present invention, the glutamic acid salt may be used in a range of 1.0 mol to 2.0 mol, based on 1 mol of the triglyceride derivative. Here, when the glutamic acid salt was used in a range of 1.0 mol to 1.3 mol based on 1 mol of the triglyceride derivative, a reaction yield was in a level of 60% to 70%, but though the reason was not confirmed, when more than 1.3 mol of the glutamic acid salt was used within the range described, the reaction yield was significantly improved to 90% or more. In particular, when more than 1.3 mol and 1.7 mol or less of the glutamic acid salt is used, a high yield characteristic is shown, which is preferred in the present invention, but is not limited thereto.

In the step of reacting with the glutamic acid salt according to an exemplary embodiment of the present invention, a temperature is not limited as long as it is equal to or lower than room temperature (23° C.), but the step may be performed under a mild condition of a temperature of preferably 0° C. to 20° C., and more preferably 5° C. to 20° C. When the temperature is out of the reaction temperature range described above, amino acid denaturation occurs to cause a problem of lowering a commercial value, such as color change and off-flavor occurrence, which is thus not preferred.

In addition, in the step of reacting with the glutamic acid salt according to an exemplary embodiment of the present invention, it was found that pH adjustment during the reaction is a key point. A phenomenon in which an acidity of pH is increased together with a high exothermic reaction during the reaction occurs. Due to the phenomenon, it is preferred to further include a step of adding a base and adjusting the pH so that the pH range described above is maintained.

It is preferred that the condensation reaction step according to an exemplary embodiment of the present invention is performed under one or more reaction solvents selected from methanol, ethanol, propyl alcohol, isopropyl alcohol, and butyl alcohol, and it is preferred to use isopropyl alcohol for not causing irritation to skin, but the present invention is not limited thereto.

Hereinafter, the present invention will be described in more detail with reference to the following Examples. However, the following Examples are only illustrative of the present invention, and do not limit the present invention.

In addition, evaluation of the solubility, foamability, biodegradability, and irritation of the glutamate-based surfactant prepared by the following method was performed by the following method, and the results are shown in Tables 1 to 3.

1. Solubility Evaluation

TurbiScane LAb (Leanontech, pulse infrared light source: 880 nm) was used to measure a transmittance of the glutamate-based surfactant prepared in Example 1. The transmittance was obtained by scanning in a longitudinal direction of a sample solution at 37° C. every 6 hours for 72 hours to measure light (135°) post-scattered (transmitted) by the sample solution. Here, as a control material, commercial sodium lauryl ether sulfate (Trade name: Sodium Lauryl Ether Sulfate 70; SLES) diluted as a 30 wt % aqueous solution was used, and a relative transmittance was determined, based on the transmittance of the control material (1.0).

2. Foamability Evaluation 180 g of water was added to 20 g of the glutamate-based surfactant prepared in Example 1, thereby preparing a sample solution having a solid content of 3 wt %. 0.05 g of an artificial sebum solution was added dropwise to the sample solution, and a SITA R-2000 foam tester (condition: 800 rpm/min, 15 times (rotating for 20 seconds each time) was used to measure a height of foam after stopping rotation of a rotor. The process was repeated three times by the same method, and an average value was determined.

3. Biodegradability Evaluation

The Organization for Economic Cooperation and Development (OECD) 301D closed bottle test (a test of evaluation for 28 days to determine whether 60% or more of a sample is biodegradable within 2 weeks from the time when the sample begins to decompose) was performed to evaluate the final biodegradability of the glutamate-based surfactant prepared in Example 1. Here, biodegradability is determined to be excellent when the final biodegradability is 60% or more.

4. Irritation Evaluation

A hen's egg chorioallantoic membrane (HET-CAM) method evaluation was used for measurement. Compositions including a commercial 30 wt % SLES aqueous solution and the glutamate-based surfactant (30 wt %) prepared in Example 1 at weight ratios of 10:0, 8:2, 6:4, 4:6, 2:8, and 0:10 were prepared and irritation of each composition was evaluated. An evaluation criterion was no irritation (0), light irritation_light erythema (1), medium irritation_even erythema in a medium degree (2), strong irritation_erythema with edema (3), strong irritation_strong erythema with edema and blister (4).

% described in the present invention indicates wt %, unless otherwise stated.

Example 1

Step 1:

To a four neck flask reactor having 1 L volume equipped with a distiller having a stirring rod, a thermometer, and a cooler attached thereto, 660 g of a triglyceride derivative derived from cocoa butter (1 mol, trade name: CNO oil) was added and heated to 70° C., and then 151.06 g (1.1 mol) of phosphorus trichloride was slowly added. After adding the phosphorus trichloride, the reactants were stirred for 6 hours. After completion of the reaction for 6 hours, stirring was stopped while the reactor temperature was maintained, thereby removing glycerol and phosphorus acid as by-products from the lower portion of the reactor, and vacuum was applied to remove residual phosphorus trichloride (670.11 g, yield=99.38%). Thereafter, the product was used in the next reaction without additional purification.

Step 2:

To a five neck flask reactor having 1 L volume equipped with a distiller having a stirring rod, a thermometer, and a cooler attached thereto, 400 g of ionized water, 75.64 g (1.4 mol) of monosodium glutamate, 140 g of NaOH (50 wt % in $H_2O$), and 200 g of isopropyl alcohol were added and dissolved (pH 12.5). A reaction temperature was maintained at 15° C., and pH change was confirmed while 100 g (1 mol) of the product prepared in step 1 was slowly added (maintaining the pH of the reaction solution is the key point). Here, as the product prepared in step 1 is added, pH is decreased with a rapid exothermic reaction, and thus, NaOH (50 wt % in $H_2O$) was further added during the reaction in order to maintain pH of 12.5. After completion of addition of the product prepared in step 1, the reaction was performed at the same temperature for 6 hours.

Step 3:

To a reactor equipped with a lower valve having a stirring rod, a thermometer, and a heating device attached thereto, the reactants of step 2 were added, the reactants were heated to 85° C., and ionized water and $H_2SO_4$ were added to convert the reactants into an organic acid form.

After the temperature reached 85° C., when stirring was stopped, the converted organic acid (upper layer) and the ionized water (lower layer) including salts (NaCl, $Na_2SO_4$) are layer-separated into upper/lower layers.

Here, the organic acid layer is positioned in the upper layer part and the ionized water layer is positioned in the lower layer, depending on the specific gravities of the organic acid layer and the ionized water layer in which salts (NaCl, $Na_2SO_4$) are dissolved.

TABLE 1

| Specific gravity (90° C.) | Specific gravity |
|---|---|
| Organic acid layer | 0.968 |
| Ionized water layer | 1.06 |

After being allowed to stand for 1 hour, the ionized water layer in the lower layer is removed through a reactor lower valve.

Thereafter, only the ionized water is added to further remove a small amount of inorganic salts (NaCl, $Na_2SO_4$) remaining in the organic acid layer three times. Here, since most of the inorganic salt was removed in the preceding removal process, the specific gravity of the ionized water layer after washing was decreased. The specific gravity of the ionized water alone at 90° C. was 0.938 which was lower than the specific gravity of the organic acid layer, and thus, the wash ionized water layer is positioned above the organic acid layer, whereby the ionized water layer could not be removed through the reactor lower valve.

Thus, a NaCl inorganic salt was optionally added to increase the specific gravity of the ionized water layer and position the ionized water layer in the reactor lower layer, thereby simplifying a washing process without the need for an additional reactor at the time of layer separation.

When NaCl was optionally added, the specific gravity of the ionized water for each concentration of NaCl was as shown in the following table 2.

The structural analysis (NMR) data of the glutamate-based surfactant prepared in Example 1 is as follows:

1H-NMR (400 MHz, $CD_3OD$): δ 4.893 (s, 1H), 3.721 (s, 2H), 2.234 (t, 2H), 1.610 (br, 2H), 1.262 (br, 18H), 0.893 (t, 3H)

13C-NMR (400 MHz, $CD_3OD$): δ 176.817, 176.011, 49.787, 49.575, 49.362, 49.937, 48.724, 48.512, 44.738, 37.321, 33.224, 30.916, 30.798, 30.659, 30.630, 30.571, 27.031, 23.887, 14.616

Example 2

The reaction was performed in the same manner as in Example 1, and in the inorganic salt removal process, the ionized water washing was performed for each concentration of NaCl listed in Table 2. Here, a wash temperature was 90° C., stirring was performed for 30 minutes, and the standing time was 1 hour.

TABLE 2

| Specific gravity (90° C.) | | Specific gravity | Layer separation |
|---|---|---|---|
| Organic acid layer | | 0.968 | — |
| Ionized water (alone) | | 0.938 | Ionized water layer positioned in upper layer |
| Specific gravity of ionized water when adding NaCl (90° C.) | 1 wt % | 1.014 | No layer separation (emulsification) |
| | 2 wt % | 1.02 | No layer separation (emulsification) |
| | 3 wt % | 1.024 | No layer separation (emulsification) |
| | 4 wt % | 1.03 | Layer separation (ionized water layer in lower layer) |
| | 5 wt % | 1.038 | Layer separation (ionized water layer in lower layer) |

As shown in Table 2, at a NaCl concentration of 4 wt % or more, the ionized water layer after washing the inorganic salt in the inorganic salt removal process was positioned in the lower portion of the reactor, thereby easily removing the ionized water layer without the need for an additional process, and at a NaCl concentration lower than 4 wt %, layer separation does not occur by emulsification, even when the specific gravity of the ionized water layer is higher than the organic acid layer, whereby it was not easy to remove the ionized water layer.

Example 3

The reaction was performed in the same manner as in Example 1 under the reaction conditions shown in Table 3 (reaction conditions of step 2), except that step 3 was not performed in Example 3, thereby obtaining the glutamate-based surfactant.

In addition, evaluation of the solubility, foamability, and biodegradability of the glutamate-based surfactants prepared by the above method was performed by the method of Example 1, and the results are shown in Tables 4 and 5.

TABLE 3

| | | Reaction temperature (° C.) | pH | Use amount of monosodium glutamate (mol[1]) | Yield (%) | FA[2](%) |
|---|---|---|---|---|---|---|
| Example | 3 | 5 | 12.5 | 1.4 | 91.84 | 3.11 |
| | 4 | 10 | 12.5 | 1.4 | 93.15 | 3.09 |
| | 5 | 15 | 12.5 | 1.4 | 93.64 | 2.87 |
| | 6 | 20 | 12.5 | 1.4 | 95.96 | 2.81 |
| | 7 | 15 | 12.0 | 1.4 | 92.12 | 2.35 |
| | 8 | 15 | 13.0 | 1.4 | 96.09 | 2.22 |
| | 9 | 15 | 12.5 | 1.0 | 63.16 | 20.57 |
| | 10 | 15 | 12.5 | 1.2 | 69.34 | 20.37 |
| | 11 | 15 | 12.5 | 1.7 | 93.51 | 2.59 |
| | 12 | 15 | 12.5 | 2.0 | 71.07 | 10.95 |
| | 13 | 25 | 12.5 | 1.4 | 49.03 | 41.25 |
| | 14 | 30 | 12.5 | 1.4 | 34.74 | 62.37 |
| | 15 | 15 | 10.0 | 1.4 | 52.82 | 43.49 |
| | 16 | 15 | 11.0 | 1.4 | 58.43 | 39.44 |

[1]based on 1 mol of triglyceride derivative
[2]free fatty acid content produced as reaction by-product As seen from Table 3, the glutamate-based surfactant may be provided with a high yield, according to the preparation method of the present invention.

However, it was found that in the reaction of step b) of reacting with the glutamic acid salt, the yield and the impurity content are varied depending on the temperature and pH.

In addition, in Examples 13 and 14, since the color of the finally obtained glutamate-based surfactant was dark yellow-brown (APHA≥10), the commercial value was lowered, which is not preferred.

TABLE 4

|  | Solubility | Foamability | Biodegradability (%) | Irritation |
|---|---|---|---|---|
| Example 3 | 1.8 | 892 | 394 | 0 |
| Example 5 | 1.8 | 824 | 345 | 0 |
| Example 9 | 1.2 | 751 | 284 | 0 |
| Example 15 | 1.1 | 726 | 128 | 0 |
| 30 wt % SLES sol | 1.0 | 687 | 52 | 1 |

TABLE 5

| 30 wt % SLES sol: Example 3 (wt:wt) | Irritation |
|---|---|
| 10:0 | 1 |
| 8:2 | 1 |
| 6:4 | 1 |
| 4:6 | 0 |
| 8:2 | 0 |
| 0:10 | 0 |

30 wt % SLES sol (Sodium laureth sulfate) As seen from Tables 4 and 5, according to the present invention, foamability equivalent to or higher than commercial surfactants as well as high solubility in water may be implemented, thereby providing high detergency. In addition, according to the present invention, an anion-based surfactant having low irritation to the human body and excellent biodegradability may be provided.

In addition, according to the present invention, a glutamate-based surfactant having excellent physical properties described above may be provided in a more competitive and environmentally friendly manner by a mild reaction process which minimizes unreacted material residues with high reactivity and does not need a complicated purification process.

The invention claimed is:

1. A method for preparing a glutamate-based surfactant, the method comprising:
    a) subjecting a triglyceride derivative to a chlorination addition reaction;
    b) reacting a product from a) with a glutamic acid salt to prepare a reaction mixture;
    c) adding an acid aqueous solution to the reaction mixture from b) to separate layers; and
    d) purifying an organic layer separated from c) with a 4 wt % or more inorganic salt aqueous solution to prepare the glutamate-based surfactant.

2. The method for preparing a glutamate-based surfactant of claim 1, wherein an inorganic salt of the inorganic salt aqueous solution is any one or two or more selected from NaCl, $Na_2SO_4$, $NaNO_3$, and $Na_3PO_4$.

3. The method for preparing a glutamate-based surfactant of claim 1, wherein the inorganic salt aqueous solution is a 4 wt % to 20 wt % solution.

4. The method for preparing a glutamate-based surfactant of claim 1, wherein the acid aqueous solution is an aqueous solution including any one or two or more selected from sulfuric acid, hydrochloric acid, phosphoric acid, and nitric acid.

5. The method for preparing a glutamate-based surfactant of claim 1, wherein the inorganic salt aqueous solution has a specific gravity of 1.03 or more.

6. The method for preparing a glutamate-based surfactant of claim 1, wherein the purifying is performed by stirring at 60° C. to 95° C. and then layer separation.

7. The method for preparing a glutamate-based surfactant of claim 1, wherein b) is performed at 0° C. to 20° C. and pH 12 to 14.

8. The method for preparing a glutamate-based surfactant of claim 1, wherein in b), the glutamic acid salt is used in a range of 1.0 mol to 2.0 mol, based on 1 mol of the triglyceride derivative.

9. The method for preparing a glutamate-based surfactant of claim 1, wherein the triglyceride derivative is obtained from one or more triglyceride-containing materials selected from shea butter, cupuacu butter, mango butter, pitch butter, lime butter, argan butter, jojoba butter, coffee butter, cocoa butter, pistachio butter, rice butter, vegetable lanolin butter, olive butter, camellia butter, aloe butter, vanilla butter, avocado butter, hemp seed butter, illipe butter, kokum butter, mochaccino butter, murumuru butter, shea aloe butter, and sweet almond butter.

10. The method for preparing a glutamate-based surfactant of claim 1, wherein the chlorination addition reaction is performed by reacting 1 mol of the triglyceride derivative with 1.0 mol to 2.0 mol of a chlorinated compound.

11. The method for preparing a glutamate-based surfactant of claim 1, wherein the chlorination addition reaction is performed with one or more chlorinated compounds selected from phosphorus pentachloride, phosphorus trichloride, and sulfonyl chloride (I).

* * * * *